(12) United States Patent
Bertaux et al.

(10) Patent No.: US 9,358,294 B2
(45) Date of Patent: Jun. 7, 2016

(54) METHOD FOR FORMULATING A VACCINE CONTAINING AT LEAST TWO ANTIGENS CAPABLE OF ADSORBING ONTO ALUMINIUM OXYHYDROXIDE

(71) Applicant: Sanofi Pasteur, Lyons (FR)

(72) Inventors: Landry Bertaux, Lyons (FR); Isabelle Chacornac, Tupin et Semons (FR); Alain Françon, Bessenay (FR); Jean-François Hau, Rouen (FR); Sandrine Lentsch Graf, Sainte Foy les Lyon (FR)

(73) Assignee: SANOFI PASTEUR, lyon (FR)

( * ) Notice: Subject to any disclaimer, the term of this patent is extended or adjusted under 35 U.S.C. 154(b) by 0 days.

(21) Appl. No.: 14/372,695

(22) PCT Filed: Jan. 17, 2013

(86) PCT No.: PCT/FR2013/050106
§ 371 (c)(1),
(2) Date: Jul. 16, 2014

(87) PCT Pub. No.: WO2013/107988
PCT Pub. Date: Jul. 25, 2013

(65) Prior Publication Data
US 2014/0370049 A1 Dec. 18, 2014

(30) Foreign Application Priority Data

Jan. 17, 2012 (FR) .................................... 12 50464

(51) Int. Cl.
| | |
|---|---|
| *A61K 39/385* | (2006.01) |
| *A61K 47/02* | (2006.01) |
| *A61K 39/12* | (2006.01) |
| *A61K 39/102* | (2006.01) |
| *A61K 39/29* | (2006.01) |
| *C12N 7/00* | (2006.01) |
| *A61K 39/05* | (2006.01) |
| *A61K 39/08* | (2006.01) |
| *A61K 39/02* | (2006.01) |
| *A61K 39/00* | (2006.01) |

(52) U.S. Cl.
CPC .................. *A61K 47/02* (2013.01); *A61K 39/05* (2013.01); *A61K 39/08* (2013.01); *A61K 39/099* (2013.01); *A61K 39/102* (2013.01); *A61K 39/12* (2013.01); *A61K 39/29* (2013.01); *C12N 7/00* (2013.01); *A61K 2039/5252* (2013.01); *A61K 2039/55505* (2013.01); *A61K 2039/70* (2013.01); *C12N 2710/00034* (2013.01); *C12N 2730/10134* (2013.01); *C12N 2770/32634* (2013.01)

(58) Field of Classification Search
CPC .................................................. A61K 47/02
See application file for complete search history.

(56) References Cited

U.S. PATENT DOCUMENTS

| | | | |
|---|---|---|---|
| 6,790,445 B1 * | 9/2004 | Ng et al. | ..................... 424/184.1 |
| 7,404,960 B2 | 7/2008 | Francon | |

FOREIGN PATENT DOCUMENTS

| | | |
|---|---|---|
| EP | 1 416 958 A1 | 5/2004 |
| WO | WO-99/13906 A1 | 3/1999 |
| WO | WO-03/009869 A1 | 2/2003 |
| WO | WO-03/013500 A1 | 2/2003 |

OTHER PUBLICATIONS

International Search Report for PCT/FR2013/050106, 3 pages (Apr. 2, 2013).
Sturgess, A.W. et al., Haemophilus influenzae type b conjugate vaccine stabilit: catalytic depolymerization of PRP in the presence of aluminum hydroxide, Vaccine, 17(9-10):1169-78 (1999).

* cited by examiner

*Primary Examiner* — Albert Navarro
(74) *Attorney, Agent, or Firm* — Proskauer Rose LLP; Fangli Chen

(57) ABSTRACT

The subject matter of the invention is a method for preparing a vaccine composition comprising at least aluminum oxyhydroxide (AlOOH), and at least the hepatitis B surface antigen and the *Haemophilus influenzae* type b antigen. According to the invention, the hepatitis B surface antigen is kept adsorbed on the AlOOH, whereas the Hib antigen is kept nonadsorbed. To this end: the hepatitis B surface antigen is adsorbed onto AlOOH in order to obtain an AlOOH/HBsAg complex, then—said AlOOH/HBsAg complex is mixed with the Hib antigen in the presence of cationic amino acids at a concentration of at least 100 mg/l, and of phosphate ions at a concentration of 35 to 45 mMol/l.

12 Claims, 1 Drawing Sheet

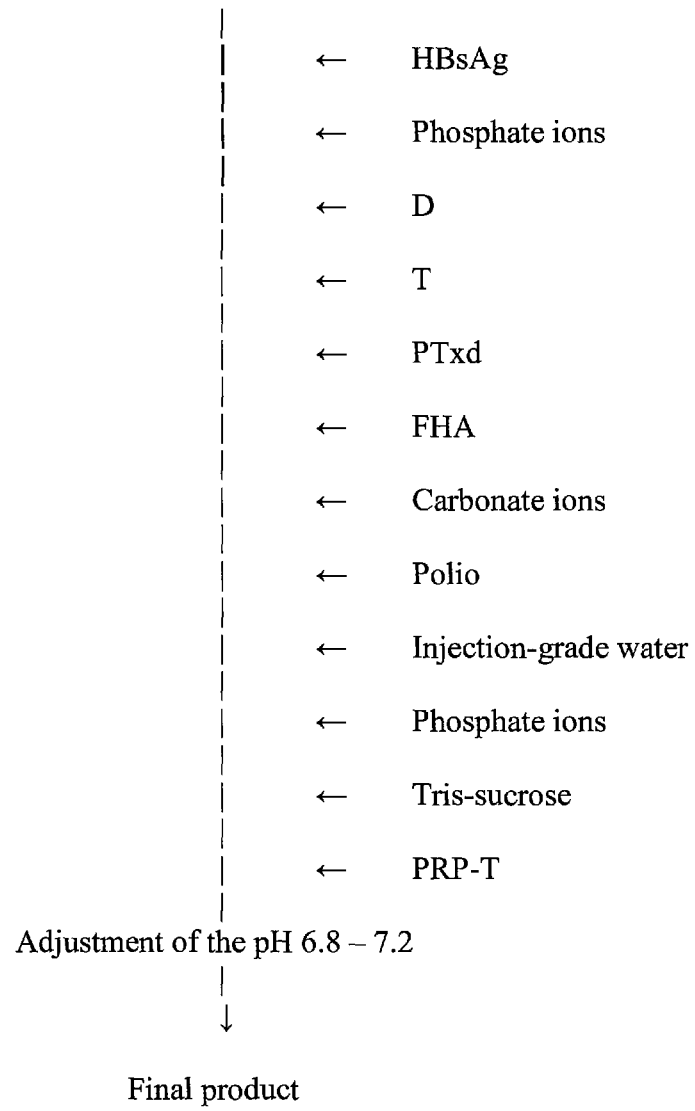

METHOD FOR FORMULATING A VACCINE CONTAINING AT LEAST TWO ANTIGENS CAPABLE OF ADSORBING ONTO ALUMINIUM OXYHYDROXIDE

CROSS REFERENCE TO RELATED APPLICATIONS

The present application is a U.S. National Phase Entry of International Application PCT/FR2013/050106 filed on Jan. 17 2013, which claims priority to Priority Application FR 12/50,464 filed on Jan. 17 2012, the disclosures of which are hereby incorporated by reference.

The invention relates to the field of vaccine combinations comprising both the hepatitis B valence consisting of the hepatitis B virus surface antigen (HBsAg) and the *Haemophilus influenzae* type b valence, consisting of its capsular polysaccharide, called polyribosylribitol phosphate (PRP), which is, in order to be effective in children under the age of two, conjugated to a carrier protein, for example the tetanus protein.

Such combinations, which are intended for administration in young children, generally comprise other antigens that make it possible to vaccinate against several diseases in a single operation, and also an aluminum-based adjuvant.

Thus, patent application WO 99/13906 discloses a vaccine composition comprising, as is described on page 13, antigens against diphtheria, tetanus, polio, whooping cough, hepatitis B and *Haemophilus influenzae* type b infections. Some of these antigens need to be adsorbed onto an aluminum salt in order to be immunogenic. This is in particular the case with the hepatitis B surface antigen or HBsAg.

However, as is indicated on page 12 of application WO 99/13906, the Hib valence, consisting of the capsular polysaccharide conjugated to the tetanus protein, has a tendency to lose its immunogenicity over time when it is adsorbed onto aluminum salts. In order to avoid this drawback, the solution proposed in this prior art is, as had already been recommended in the prior application PCT/FR96/00791, to add anions and in particular phosphate, carbonate or citrate ions.

However, the authors of the present invention have noted that, while the addition of ions, in particular of phosphates or of carbonates, actually makes it possible to prevent the adsorption of PRP-T onto aluminum oxide hydroxide (AlOOH), and therefore to maintain its immunogenicity over time, this addition also has the drawback of desorbing the hepatitis B surface antigen when the latter has, itself, also been adsorbed onto aluminum oxide hydroxide.

It is therefore necessary to find a method for preparing a vaccine combination comprising aluminum oxide hydroxide, in which the hepatitis B surface antigen is kept adsorbed on AlOOH, whereas the Hib antigen is kept nonadsorbed.

To this end, the subject of the present invention is a method for preparing a liquid vaccine combination comprising at least:
  one hepatitis B surface antigen (HBsAg),
  one *Haemophilus influenzae* type b (Hib) antigen consisting of capsular polysaccharide conjugated to a carrier protein,
  aluminum oxide hydroxide (AlOOH),
in which the hepatitis B surface antigen is kept adsorbed on AlOOH, whereas the Hib antigen is kept nonadsorbed, wherein:
  the hepatitis B surface antigen is adsorbed onto AlOOH in order to obtain an AlOOH/HBsAg complex,
  said AlOOH/HBsAg complex is mixed with the Hib antigen in the presence of cationic amino acids at a concentration of at least 100 mg/l and of phosphate ions at a concentration of 35 to 45 mMol/l.

By virtue of the method according to the invention, it is possible to achieve the desired balance between keeping the adsorption of the hepatitis B surface antigen on the aluminum oxide hydroxide and keeping the nonadsorption of the Hib antigen.

According to one particular embodiment of the invention, the HBsAg antigen is adsorbed onto the aluminum by mixing a suspension of AlOOH with a suspension of HBsAg with stirring for at least 4 hours, preferably at least 12 hours, preferably between 20 and 24 hours.

According to one particular embodiment of the invention, the cationic amino acids are added to said AlOOH/HBsAg complex before the mixing with the Hib antigen.

According to an alternative embodiment of the invention, the cationic amino acids are added to said Hib antigen before the mixing with the AlOOH/HBsAg complex.

According to one embodiment of the invention, the phosphate ions are added to said AlOOH/HBsAg complex before the mixing with the Hib antigen.

According to one embodiment of the invention, the pH of the preparation comprising the AlOOH/HBsAg complex is adjusted to 7.1±0.1 before the mixing with the Hib antigen.

The subject of the invention is also a vaccine combination obtained according to the method claimed and comprising at least:
  the hepatitis B surface antigen,
  the diphtheria antigen in the form of diphtheria toxin D,
  the tetanus antigen in the form of tetanus toxin T,
  the whooping cough antigens in the form of Purified Toxin (PTxd) and of Filamentous Hemagglutinin (FHA),
  the *Haemophilus influenzae* type b antigen, in the form of polyribosylribitol phosphate conjugated to the tetanus protein (PRP-T),
  the polio antigens in the form of inactivated type 1, 2 and 3 viruses.

Such a vaccine composition has the advantage of being in liquid form, thereby avoiding operations to take up the lyophilisate; it has proven to be sufficiently stable to remain immunogenic until the day it is used, even 36 months after its date of manufacture.

According to the invention, the vaccine composition comprises a hepatitis B surface antigen (HBsAg). This antigen may in particular be a hepatitis B surface antigen such as the one present in the Recombivax HB™ vaccine, or in any other hepatitis B vaccine. It may in particular be the recombinant antigen obtained by fermentation of a *Hansenula polymorpha* yeast which has been modified, according to the technology developed by Crucell, such as the one present in the Hepavax-Gene™ vaccine. For the purposes of the invention, the amount of HBsAg present in a 0.5 ml dose is advantageously between 5 and 15 µg, and in particular 10 µg.

According to the invention, the vaccine composition comprises a *Haemophilus influenzae* type b (Hib) antigen. This antigen consists of the capsular polysaccharide of the bacterium or PolyribosylRibitol Phosphate (PRP) which is conjugated to a carrier protein. The carrier protein may be any protein used in this respect in the vaccine field. It may be, for example, diphtheria toxin D, tetanus toxin T, *Haemophilus influenzae* lipoprotein D, CRM197 or the *N. meningitidis* outer membrane protein (OMP). Use is preferably made of the tetanus protein in order to obtain the PRP-T conjugate. For the purposes of the present invention, the PRP-T conjugate may be present in a proportion of from 1 to 30 µg of PRP per 0.5 ml dose; advantageously from 5 to 25 µg of PRP per dose; preferably from 10 to 15 µg of PRP per dose; entirely preferably from 10 to 12 µg of PRP per dose, and more particularly 12 µg of PRP, conjugated to 22-36 µg of tetanus protein.

According to the invention, the vaccine composition comprises aluminum oxide hydroxide AlOOH. This aluminum salt is very commonly incorrectly called aluminum hydroxide. The AlOOH which can be used for the purposes of the present invention may be, for example, the AlOOH salt sold by Brenntag AG, or Rehydragel HPA from Reheis Corp. (Berkeley Heights, N.J.), although the method of production of each of the two adjuvants differs. The amount of AlOOH used is calculated so as to allow a satisfactory immune response to be achieved; it depends in particular on the number and on the nature of the antigens present in the composition and also on the amount of each of these antigens.

Purely by way of information, the maximum adsorption of HBsAg onto AlOOH is about 780 µg of protein per mg of aluminum (conventionally, the amount of AlOOH is expressed as amount of aluminum $Al^{3+}$). For a vaccine dose comprising 10 µg of HBsAg, without any other additional antigens, 13 µg of aluminum would thus suffice, which is an amount that is however insufficient to obtain the desired efficacy when other antigens are added. Thus, depending on the addition of one or more additional antigens, 10 µg of HBsAg may be brought into contact with from 0.01 mg to 1.25 mg of aluminum, which is the maximum amount recommended by the European pharmacopeia.

For example, a 0.5 ml dose of a pediatric vaccine comprising diphtheria, tetanus, whooping cough and hepatitis B antigens may conventionally contain from 0.5 to 0.7 mg of aluminum, preferably approximately 0.6 mg of aluminum.

According to the invention, the hepatitis B surface antigen is kept adsorbed on AlOOH, which means that at least 60%, preferably at least 65%, preferably at least 70%, preferably at least 75%, preferably at least 80%, preferably at least 85%, preferably at least 90%, preferably at least 95% of the total amount of this antigen present in the composition is present in adsorbed form.

According to the invention, the Hib antigen is kept nonadsorbed on AlOOH, which means that at least 65%, preferably at least 70%, preferably at least 75% of the total amount of this antigen present in the composition is present in nonadsorbed form.

According to the invention, the period of time during which the hepatitis B surface antigen is kept adsorbed on the AlOOH and the Hib antigen is kept nonadsorbed is at least 3 months, preferably at least 6 months, preferably at least 12 months, preferably at least 18 months, preferably at least 24 months, more preferably at least 36 months starting from the date of manufacture of the composition, when the storage temperature is 5±3° C. Preferably, the amount of adsorbed or nonadsorbed antigens is stable over time, but it may also vary, provided that it remains within acceptable limits. Thus, when at least 85% of the total amount of the HBsAg present in the composition is adsorbed on the AlOOH for 3 months starting from the date of manufacture of the composition stored at a temperature of 5±3° C., it is entirely possible that, after one year and still under the same storage conditions, 80% of the total amount of the HBsAg present in the composition is kept adsorbed.

In order to assess the amount of antigen adsorbed, those skilled in the art may use any known method.

With regard to the determination of the percentage adsorption of the HBsAg, it is possible to use a sandwich ELISA method according to the rules defined by the European pharmacopeia 2.7.1. Briefly, the HBsAg is captured by an anti-HBsAg primary monoclonal antibody of IgM type, in wells of a 96-well plate. The HBsAg thus bound is coated with an anti-HBsAg secondary monoclonal antibody, of IgG type, which is itself detected by means of a peroxidase-coupled anti-IgG polyclonal antibody. A chromogenic substrate for peroxidase, tetramethylbenzidine (TMB), serves as a developing agent. When it is added, a color develops, the intensity of which is proportional to the amount of HBsAg captured in the well. The results are analyzed according to the parallel line method described in the European pharmacopeia 5.3.3. The percentage adsorption is obtained from the determination of the total HBsAg content and of the nonadsorbed HBsAg content.

With regard to the amount of nonadsorbed PRP-T, the evaluation can be carried out by HPAEC-PAD (high-performance ion exchange chromatography-pulsed amperometric detection).

According to the method of the invention, the hepatitis B surface antigen is adsorbed onto AlOOH. This step can be carried out by bringing the hepatitis B surface antigen and the AlOOH into contact in the absence of any other antigen and allowing the hepatitis B surface antigen to adsorb onto the AlOOH for at least 4 hours, preferably at least 12 hours, entirely preferably between 20 and 24 hours, so as to obtain a preparation containing an AlOOH/HBsAg complex. This adsorption can be carried out, according to the invention, in the absence of phosphate ions. The objective pursued by means of a prolonged contact time between the hepatitis B surface antigen and the AlOOH consists in maximizing electrostatic interactions and in promoting stable interactions, which can thus result in adsorption by ligand exchange. This contact is advantageously continued with stirring.

According to the method of the invention, the AlOOH/HBsAg complex is mixed with the Hib antigen in the presence of cationic amino acids and of phosphate ions.

For the purposes of the invention, the term "cationic amino acids" is intended to mean amino acids of which the pHi is higher than the pH of the vaccine composition and which will therefore be in cationic form at the pH of the vaccine; these are in particular Lysine (Lys), Arginine (Arg) or Histidine (His); each of these amino acids can be used alone, as a mixture either in pairs (Lys+Arg; Lys+His; Arg+His) or all 3 together (Lys+Arg+His). According to one particular embodiment, the cationic amino acids may be associated in dipeptide form. Mention may particularly be made of the dipeptides Lys-Lys, Lys-Arg, Lys-His, Arg-Arg, Arg-Lys, Arg-His, His-His, His-Lys and His-Arg. Alternatively, a dipeptide of use for the purposes of the present invention may be composed of a cationic amino acid and of an uncharged amino acid selected from Ala, Val, Leu, Iso, Pro, Met, Phe, Trp, Gly, Ser, Thr, Cys, Tyr, Asp and Gln. Thus, in practice, a preparation containing one or more cationic amino acid(s) in free and/or dipeptide form may be used. It is also possible to use amino acid preparations comprising cationic amino acids in desired amount, as a mixture with other amino acids. In order not to produce too great a drop in the pH during the addition of the amino acids, it is possible to envision increasing the pH of the preparation comprising the amino acids before adding it to the AlOOH/HBsAg complex, by means of a base, in particular sodium hydroxide.

According to the invention, the amount of cationic amino acids ultimately present in the vaccine composition must be at least 100 mg/l, advantageously at least 300 mg/l, advantageously at least 400 mg/l, entirely preferably at least 500 mg/l. There is no critical maximum dose. However, it is preferable for the maximum amount to be at most 2 mg/ml, more preferably at most 1 mg/ml, more preferably at most 800 µg/ml, entirely preferably at most 700 µg/ml. When calculating the amount of cationic amino acids to be added, the cationic amino acids that may be introduced by the media in which the antigens other than HBsAg and the Hib antigen present should be taken into account.

According to one alternative of the method, it is possible to determine the amount of cationic amino acids relative to the weight of the Hib capsular polysaccharide and to provide for a Hib polysaccharide/cationic amino acid weight ratio of 1:4 to 1:100, advantageously of 1:10 to 1:80, preferably of 1:15 to 1:60, or particularly preferably of 1:20 to 1:30 or 40.

According to the method of the invention, the AlOOH/HBsAg complex is mixed with the Hib antigen in the presence of cationic amino acids, but also in the presence of phosphate ions. According to one embodiment of the invention, the phosphate ions are added to the AlOOH/HBsAg complex before it is brought into contact with the Hib antigen. The phosphate ions can, for example, be introduced by adding sodium hydrogen phosphate or potassium hydrogen phosphate, or else a mixture of the two. The amount of phosphate ions is calculated so that the maximum amount of hepatitis B surface antigens remains adsorbed on the AlOOH while at the same time avoiding the adsorption of the Hib antigen. This amount varies according to the nature and the number of the antigens present, and in particular according to the antigens other than the HBsAg and Hib antigens.

Thus, for a vaccine combination comprising the antigens normally used in pediatric vaccines, that is to say, in addition to the HBsAg and the Hib antigen, the diphtheria, tetanus and whooping cough antigens, it may be advantageous to add phosphate ions such that the phosphate ion concentration in the vaccine composition ultimately obtained is at least equal to 35 mMol/l, and more particularly is between 35 and 45 mMol/l, limits included; preferably between 38 and 44 mMol/l, limits included; entirely preferably between 38 and 42 mMol/l, limits included. According to one preferred embodiment, the phosphate ion concentration in the vaccine composition finally obtained is 40 mMol/l.

According to an alternative embodiment, the phosphate ions are added in an amount such that they are present in the vaccine composition at a final concentration of between 35 and 38 mMol/l, limits included. This is completed by also adding carbonate ions, but in a limited amount however, since it has in fact been noted that an excessive amount of carbonate ions is unfavorable. Advantageously, they may be added in an amount such that they are present in the vaccine composition at a final concentration of less than or equal to 10 mMol/l.

In order to avoid an excessive ionic shock which could destabilise the HBsAg and promote desorption thereof, it is recommended to add the phosphate ions in several (example in 2) distinct operations (steps). Thus, the phosphate ions may be added in a first operation, in an amount which makes it possible to achieve a final concentration of between 20 and 30 mMol/l, limits included; then, in a second operation, in an amount which makes it possible to achieve a final concentration as specified above.

According to one preferred embodiment of the method according to the invention, the pH of the preparation obtained is in addition adjusted to 7.1±0.1, before mixing the Hib antigen with the AlOOH/HBsAg complex. It has in fact been noted that such a pH value has a positive effect on keeping the Hib antigen in the nonadsorbed state.

According to one particular embodiment, the pH is in addition adjusted to 7.1±0.1 after the mixing phase.

Thus, by virtue of the method according to the invention, it is possible to obtain a vaccine composition in which:

(i) at least 60% or 80%, preferably at least 85%, of the total amount of the hepatitis B surface antigen present in the composition is adsorbed on the AlOOH for at least 3 months starting from the date of manufacture of the composition stored at a temperature of 5±3° C.; and
(ii) at least 65%, 70% or 75% of the total amount of the Hib antigen present in the composition is not adsorbed on the AlOOH.

The expression "AlOOH/HBsAg complex" should be interpreted as meaning that the complex comprises at least the HBsAg antigen adsorbed on AlOOH. The complex may contain other antigens, whether that is specified or not.

One or more additional antigens may in addition come to form the complex. They may in particular be diphtheria toxoid (D), tetanus toxoid (T), whooping cough acellular antigens such as: *Bordetella pertussis* detoxified toxin (PTxd), filamentous hemagglutinin (FHA), pertactin (69 kDa antigen) and agglutinogens (fimbriae) of this same bacterium. According to one particularly advantageous embodiment, D, T, PTxd and FHA antigens may be added in order to form the complex.

The additional antigens may be added in various ways. They may be added sequentially following the hepatitis B surface antigen preadsorbed (i) either onto the total amount of AlOOH that needs to be present in the vaccine composition; (ii) or onto a partial amount, subsequently added to in order to reach the total amount. Alternatively, the additional antigens may be adsorbed separately, each onto a partial amount of AlOOH just like the HBsAg. A mixed adsorption process may also be provided for—some antigens being adsorbed separately, others being adsorbed sequentially.

According to one particular embodiment of the method according to the invention, the composition obtained is stirred after the addition of each antigen.

According to one advantageous embodiment, given only by way of example, the HBsAg is adsorbed separately onto a partial amount of AlOOH corresponding to approximately 30% (one third) of the total amount of AlOOH present in the final composition. In parallel, the D and T antigens are sequentially adsorbed onto the additional part of the AlOOH. The PTxd and FHA whooping cough antigens are then added to the preparation containing the AlOOH-D-T complex, each of these two whooping cough antigens themselves having been individually preadsorbed onto AlOOH. Finally, the two preparations (AlOOH-HBsAg complex and AlOOH-D-T-PTxd-FHA complex) are combined so as to form a preparation comprising the AlOOH-HBsAg-D-T-PTxd-FHA in which the amounts of each of the elements have been chosen so to obtain vaccine doses of 0.5 ml comprising, conventionally:

from 5 to 15 µg of HBsAg/dose; preferably 10 µg/dose,
from 20 to 40 Lf of D/dose; preferably from 25 to 35 Lf/dose; entirely preferably 30 Lf/dose (Lf=limit of flocculation) (expressed in another way, the amount of D is greater than or equal to 20 IU/dose),
from 5 to 25 Lf of T/dose; preferably from 10 to 15 Lf/dose; entirely preferably 10 Lf/dose (expressed in another way, the amount of T is greater than or equal to 40 IU/dose),
from 20 to 30 µg of FHA/dose; preferably 25 µg/dose,
from 20 to 30 µg of PTxd/dose; preferably 25 µg/dose.

According to one particular embodiment of the invention, polio antigens, which conventionally consist of inactivating viruses, are also added. It can be envisioned to add polioviruses of the 3 types usually present in pediatric vaccines, i.e. types 1, 2 or 3, or else, in the case where it would not be necessary to vaccinate against the 3 types, to introduce only the types against which protection is sought. The amounts of poliovirus per dose may in particular be:

between 20 and 43 DU (D antigen units), in particular 40 for type 1,
between 5 and 9 DU, in particular 8, for type 2,
between 17 and 36 DU, in particular 32, for type 3.

These antigens are not necessarily preadsorbed onto an aluminum salt before being added to the vaccine preparation.

According to one particular embodiment, the method according to the invention is a method wherein:

(i) (a) the HBsAg and the AlOOH are brought into contact in the absence of any other antigen, and the HBsAg is allowed to adsorb onto the AlOOH for at least 4 hours, preferably at least 12 hours, entirely preferably approximately 24 hours, so as to obtain a preparation containing an AlOOH/HBsAg complex;

(i) (b) a preparation comprising the D, T, PTxd and FHA antigens, preadsorbed onto AlOOH, and optionally additional *Bordetella pertussis* antigens such as pertactin and agglutinogens, is added to the preparation obtained in point (i) (a);

(ii) phosphate ions are added to the preparation obtained in point (i) (b) in order to obtain a final concentration in the vaccine of 40 mMol/l;

(iii) polio antigens are optionally added to the preparation obtained in point (ii);

(iv) a preparation containing the Hib antigen is added to the preparation obtained in point (ii) or (iii);

(v) the pH is adjusted to 7.1±0.1; and (vi) (a) at least one cationic amino acid is added so as to complete the preparation obtained in point (ii) or (iii) before the addition of the Hib antigen, or (b) at least one cationic amino acid is added to the Hib antigen;

said cationic amino acid being added in an amount sufficient to obtain a final concentration in the vaccine of at least 100 mg/l.

According to one particular embodiment, the vaccine composition according to the invention is a composition comprising HBsAg, diphtheria toxin D, tetanus toxin T, the PTxd and FHA whooping cough antigens having been preadsorbed onto AlOOH, the Hib antigen and, optionally, the polio valence, in which:

(i) at least 85%, preferably at least 90%, of the total amount of the HBsAg present in the composition is kept adsorbed on the AlOOH for at least 3 months starting from the date of manufacture of the composition stored at a temperature of 5±3° C.; and (ii) at least 65%, 70% or preferably 75% of the total amount of the Hib antigen present in the composition is not adsorbed on the AlOOH, this amount remaining relatively stable over time.

In addition, by virtue of the method according to the invention, the antigens other than HBsAg which showed that it was advantageous for them to be adsorbed onto aluminum oxide hydroxide in order to be immunogenic, are also kept adsorbed.

Thus, it is indicated, by way of example, that a composition according to the invention may comprise:

from 10 to 30 µg of HBsAg/ml; preferably 20 µg/ml;
from 40 to 80 Lf of D/ml, preferably from 50 to 70 Lf/ml;
from 10 to 50 Lf of T/ml, preferably from 10 to 30 Lf/ml;
from 40 to 60 µg of FHA/ml; preferably 50 µg/ml;
from 40 to 60 µg of PTxd/ml; preferably 50 µg/ml;
from 2 to 60 µg of PRP/ml; preferably 20-24 µg/ml;
from 1 to 2 mg of AlOOH/ml; preferably 1.2 mg of AlOOH/ml;
phosphate ions at a concentration of 35 to 45 mMol/l, preferably from 38 to 42 mMol/l of phosphate ions;
from 100 to 1000 µg/ml of cationic amino acids, preferably from 400 to 800 µg/ml; and optionally
poliovirus types 1, 2 and 3 in inactivated form, in a respective amount of 80, 16 and 64 DU/ml.

As previously indicated, a composition according to the invention may also comprise additional *Bordetella pertussis* antigens, such as pertactin (of 69 kDa) or agglutinogens.

DESCRIPTION OF THE FIGURE

FIG. 1 is a scheme of a prior art method wherein mixing is carried out after the addition of each component.

EXAMPLE

Industrial-Scale Preparation of a Bulk (250 l) of a HepB-Dt-Tt-*Pertussis*-Polio-HiB Hexavalent Vaccine This preparation is carried out under sterile conditions and with continuous stirring.

A—Preparation of HBsAg Adsorbed onto AlOOH

A homogeneous suspension of aluminum oxide hydroxide (AlOOH) gel sold by Brenntag AG, at 8 g of aluminum/l, is introduced aseptically into a 50 l tank.

After filtration through a 0.22 µm filter, the volume of HBsAg required to obtain a concentration of 20 µg/ml in the final vaccine is continuously added to the tank already containing the AlOOH.

The mixture is left to stir for 20 to 24 hours at ambient temperature so as to obtain a homogeneous suspension.

B—Preparation of D+T+PTxd+FHA Adsorbed onto Aluminum Gel

In parallel, a mixture of aluminum gel, diphtheria toxoid (D), tetanus toxoid (T), *Bordetella pertussis* toxoid (PTxd) and *Bordetella pertussis* filamentous hemagglutinin (FHA) is prepared in the following way:

A homogeneous suspension of AlOOH gel sold by Brenntag AG, at 8 g of aluminum/l, is introduced aseptically into a 250 l tank.

The solutions of D and then, after homogenization, of T are successively introduced, after filtration through a 0.22 µm filter, into the 250 l tank already containing the AlOOH, in order to obtain respective D and T concentrations in the final vaccine of 60 Lf (limit of flocculation)/ml and 20 Lf/ml.

Once the homogeneous mixture has been obtained, the suspension of PTxd preadsorbed onto AlOOH and then the suspension of FHA preadsorbed onto AlOOH are successively added aseptically into this tank, in order to obtain PTxd and FHA concentrations in the final vaccine of 25 µg/ml.

Finally, the volume of 500 mM of phosphate buffer required to obtain a phosphate ion concentration of 20 to 30 mMol/l is added after filtration through a 0.22 µm filter.

The resulting D-T-PTxd-FHA-AlOOH suspension is left to stir for at least 14 hours at a temperature of 5±3° C.

C—Preparation of the Mixture of HBsAg+D+T+PTxd+FHA Adsorbed onto Aluminum Gel

The preparation obtained in point A is added aseptically to the preparation obtained in point B.

This mixture is left to stir so as to obtain a homogeneous suspension.

The volume of 500 mM phosphate buffer required to obtain a phosphate ion concentration of 40 mMol/l in the final composition is then added after filtration through a 0.22 µm filter.

D—Saturation of the Electrostatic Sites of the Aluminum Gel/HBsAg+D+T+PTxd+FHA Complex with a Solution of Amino Acids A solution of amino acids containing 12 essential amino acids, having the following composition, is prepared:

| | |
|---|---|
| Arginine hydrochloride | 2.1 g/l, i.e. 1.73 g/l of arginine |
| Cystine | 1.2 g/l |
| Histidine | 0.8 g/l |
| Isoleucine | 2.6 g/l |
| Leucine | 2.6 g/l |
| Lysine hydrochloride | 3.65 g/l, i.e. 2.91 g/l of lysine |
| Methionine | 0.75 g/l |
| Phenylalanine | 1.65 g/l |
| Threonine | 2.4 g/l |
| Tryptophan | 0.4 g/l |
| Tyrosine | 1.8 g/l |
| Valine | 2.35 g/l |

That is to say 21.2 g/l of amino acids, including 5.44 g/l of cationic amino acids (His-Arg-Lys).

450 ml of 2.5 N sodium hydroxide (NaOH) are added (0.5 l/min) The homogenization is allowed to continue with stirring for 10 min.

This amino acid solution, filtered through a 0.22 μm filter, is continuously added to the mixture obtained in C, so as to obtain a concentration of 572 μg/ml of cationic amino acids in the final composition.

E—pH Adjustment

The pH of the suspension obtained in point D is adjusted to pH 7.1 (7.0-7.2) using a filtered stock solution of sodium hydroxide at 2.5 N.

F—Addition of the Polio Antigens

A preparation containing poliovirus serotypes 1, 2 and 3 in inactivated form (Mahoney, MEF-1 and Saukett strains, respectively), filtered through a 0.22 μm filter, is then introduced into the tank containing the suspension obtained in E.

G—Addition of PRP-T

An intermediate solution of PRP-T is first of all prepared in the following way: Tris-sucrose buffer, filtered beforehand through a 0.22 μm filter, is added to a preparation of PRP-T filtered through a 0.22 μm filter, so as to constitute an intermediate mixture.

This mixture is introduced aseptically into the mixture obtained in F.

H—Final Adjustment Phase

After homogenization of the suspension obtained in G, an amount of prefiltered injection-grade water sufficient to reach the target volume of 250 l is added. Then, if necessary, the pH of the mixture is adjusted to pH 7.1±0.1 by adding a prefiltered 2.5 N sodium hydroxide or 10% acetic acid solution.

The mixture is stored at 5±3° C., then distributed into syringes or bottles in a proportion of 0.5 ml/dose.

One 0.5 ml dose thus contains 600 μg of $Al^{3+}$, 10 μg of HBsAg, no less than 20 IU of D, no less than 40 IU of T, 25 μg of Pt, 25 μg of FHA, between 20 and 43 DU (D antigen units) of polio type 1, between 5 and 9 DU of polio type 2, between 17 and 36 DU of polio type 3, 12 μg of PRP (in the form of PRP-T), phosphate ions at a concentration of 40 mMol/l Tris-sucrose buffer at a concentration of 2.5 mMol/l of Tris and of 2.125% of sucrose, and also 286 μg of cationic amino acids (His-Arg-Lys).

Clinical Trial

The vaccine composition prepared according to the example above was tested in a clinical trial, compared to a hexavalent vaccine already present on the market, called Infanrix Hexa™, which makes it possible to vaccinate children against the same diseases as the vaccine prepared according to the invention (diphtheria, tetanus, whooping cough, polio, Hib infections and hepatitis B), but which has in particular the drawback that a part of it is lyophilized and therefore requires an operation to take up the lyophilisate prior to the administration procedure.

During the clinical trial, the 2 types of vaccine compositions were administered to children, in a vaccine scheme comprising 3 doses administered at 2, 4 and 6 months. The liquid vaccine prepared according to the method of the invention proved to be very well tolerated, and as immunogenic as the vaccine present on the market.

Experimental Data

Percentage Adsorption of HBsAg/Amount of Nonadsorbed PRP-T

Three batches of final bulk product (PFV39-41-42) and also three batches distributed into bottles (S12-13-14)—all the batches having been obtained according to the example provided were stored at +5° C. and analyzed at various times over a period of 9 and 22 months, respectively. The analysis related to the percentage adsorption of HBsAg and the amount of nonadsorbed PRP-T.

The percentage adsorption of the HBsAg was determined, as was previously indicated, from the total HBsAg content and the nonadsorbed HBsAg content, the HBsAg determination being carried out using a sandwich ELISA method according to the rules defined by the European pharmacopeia 2.7.1. Briefly, the HBsAg was captured by an anti-HBsAg primary monoclonal antibody of IgM type, in wells of a 96-well plate. The HBsAg thus bound was coated with an anti-HBsAg secondary monoclonal antibody, of IgG type, which was itself detected by means of a peroxidase-coupled anti-IgG polyclonal antibody. A chromogenic substrate for peroxidase, tetramethylbenzidine (TMB), served as a developing agent. When it was added, a color developed, the intensity of which was proportional to the amount of HBsAg captured in the well. The results were analyzed according to the parallel line method described in the European pharmacopeia 5.3.3.

In order to determine the percentage adsorption of the HBsAg, the vaccine was subjected to centrifugation (8800 g; 5 min; 20° C.), which made it possible to recover the supernatant containing the nonadsorbed HBsAg. The samples of supernatants to be tested were diluted in ELISA buffer comprising a desorption buffer, in 2-fold serial dilutions in a range included, for example, between 1/400 and 1/12 800.

The total-vaccine and standard-range samples were diluted in ELISA buffer comprising a desorption buffer, in 2-fold serial dilutions in a range included, for example, between 1/8 and 1/25 600.

A 96-well plate coated with the primary monoclonal antibody was incubated for 12 h at 5° C. and then washed with a PBS-Tween 20 solution. The dilutions of the supernatants, of the total vaccine and of the standard range were distributed into the wells. The secondary antibody was then added and the developing was carried out with the peroxidase-conjugated antibody and TMB (tetramethylbenzidine). The reaction was stopped by adding 1 N HCl. After each step, the plate was incubated for 30 min at 25° C. and then subsequently washed with the PBS-Tween 20 solution. A blank (dilution buffer) was added to the available wells and underwent the same treatments. The plate was read at OD 450 and 630 nm.

The amount of nonadsorbed PRP-T was evaluated by HPAEC-PAD (high performance anion exchange chromatography pulsed amperometric detection) in the following way:

A standard range of reference PRP-T of 0.5 to 12.5 μg/ml was first of all prepared.

The samples to be tested and also the standard-range samples were centrifuged at 5000 g for 5 min at ambient temperature. The supernatants were collected and then hydrolyzed with a 1.5 N NaCl solution containing glucosamine-1-phosphate as internal standard. A blank (0.9% NaCl; 1.5 N NaOH+internal standard) was added.

The chromatography was carried out with a mobile phase composed of 35 mM NaOH and 114 mM of sodium acetate, injected into the column at a rate of 1.2 ml/min.

The concentration of nonadsorbed PRP (µg/ml) was calculated using the following equality:

(Surface area of the PRP peak/surface area of the internal standard peak)=$a$×[PRP concentration]+$b$ in which "$a$" is the slope and "$b$" is the intercept on the y-axis, $a$ and $b$ having been determined from the regression line.

The results are given in the 4 tables below:

| Percentage adsorption of HBsAg in the formulation of the final bulk product (PVF 39-41-42) at +5° C. | | | |
|---|---|---|---|
| Time elapsed after the formulating operation | PFV39 | PFV41 | PFV42 |
| 0 | 95 | 97 | 98 |
| 1 month | 92 | 93 | 95 |
| 2 months | 92 | 92 | 93 |
| 3 months | 91 | 90 | 91 |
| 4 months | 89 | 90 | 92 |
| 5 months | 85 | 88 | 91 |
| 6 months | 89 | 88 | 89 |
| 9 months | 88 | 86 | 91 |

| Percentage adsorption of HBsAg in the formulation stored in bottles (batches S12-S13-S14) at +5° C. | | | |
|---|---|---|---|
| Time elapsed after the formulating operation | S12 | S13 | S14 |
| 0 | 95 | 97 | 98 |
| 4 months | 88 | 88 | 90 |
| 5 months | 85 | 86 | 88 |
| 7 months | 85 | 80 | 86 |
| 10 months | 83 | 84 | 87 |
| 13 months | 82 | 86 | 84 |
| 16 months | 81 | 83 | 85 |
| 22 months | 83 | 78 | 86 |

| Nonadsorbed PRP-T (µg/ml) in the formulation of the final bulk product (PVF 39-41-42) at +5° C. | | | |
|---|---|---|---|
| Time elapsed after the formulating operation | PFV39 | PFV41 | PFV42 |
| 0 | 22.6 | 20.0 | 21.0 |
| 1 month | 23.1 | 19.5 | 20.4 |
| 2 months | 23.3 | 21.6 | 22.0 |
| 3 months | 24.9 | 22.6 | 23.1 |
| 4 months | 24.2 | 22.0 | 20.7 |
| 5 months | 22.2 | 22.7 | 24.5 |
| 6 months | 27.7 | 22.9 | 21.6 |
| 9 months | 27.0 | 24.8 | 23 |

| Nonadsorbed PRP-T (µg/ml) in the formulation stored in bottles (batches S12-S13-S14) at +5° C. | | | |
|---|---|---|---|
| Time elapsed after the formulating operation | S12 | S13 | S14 |
| 0 | 22.6 | 20.0 | 21.0 |
| 4 months | 21.1 | 21.1 | 19.8 |
| 5 months | 23.0 | 19.6 | 18.6 |
| 7 months | 23.1 | 21.0 | 19.5 |
| 10 months | 25.0 | 23.4 | 21.8 |
| 13 months | 24.6 | 22.6 | 20.8 |
| 16 months | 23.5 | 22.3 | 20.8 |
| 22 months | 23.9 | 22.0 | 19.9 |

For comparison, the adsorption over time of the HBsAg contained in three batches of final bulk product (FDN5-6-7) and also in three batches distributed into bottles (S 44-45-46), of a liquid preparation composed of the same antigens but obtained according to a linear formulation method described in FIG. 1 and therefore different than that described in the example above, was also tested. This preparation contained, in 0.5 ml: 10 µg of HBsAg, 30 Lf of Dt, 10 Lf of Tt, 25 µg of Pt, 25 µg of FHA, 40 DU of poliovirus type 1, 8 DU of poliovirus type 2, 32 DU of poliovirus type 3, 12 µg of PRP (in the form of PRP-T), 0.6 mg of Al, phosphate ions at a concentration of 55 mMol/l, carbonate ions at a concentration of 20 mMol/l, Tris-sucrose buffer at a concentration of 2.5 mMol/l with respect to Tris and 2.125% with respect to sucrose, and 14 µg of cationic amino acids (His-Arg-Lys) originating from the M199 medium (polio valence), pH 6.8-7.2.

The results obtained were the following:

| Percentage adsorption of HBsAg in the formulation of the final bulk product (FDN5-6-7) at +5° C. | | | |
|---|---|---|---|
| Time elapsed after the formulating operation | FDN5 | FDN6 | FDN7 |
| 0 | 81 | 85 | 81 |
| 1 month | 78 | 82 | 62 |
| 2 months | 74 | 78 | 63 |
| 3 months | 66 | 84 | 62 |
| 6 months | 61 | 77 | 61 |

| Percentage adsorption of HBsAg in the formulation stored in bottles (batches S44-S45-S46) at +5° C. | | | |
|---|---|---|---|
| Time elapsed after the formulating operation | S44 | S45 | S46 |
| 0 | 81 | 85 | 81 |
| 7 months | 63 | 64 | 77 |
| 10 months | 57 | 65 | 51 |
| 13 months | 47 | 54 | 53 |
| 16 months | 33 | 56 | 38 |
| 22 months | 44 | 47 | 36 |
| 28 months | 44 | 51 | 44 |
| 34 months | 45 | 54 | 42 |
| 40 months | 49 | 52 | 48 |

The amounts of nonadsorbed PRP-T measured over the same period showed that there was little variation compared with time 0, and were therefore satisfactory. However, these results show that, in this case, which does not correspond to a formulation obtained by virtue of a method according to the invention, the hepatitis B surface antigen did not remain adsorbed on the aluminum oxide hydroxide.

Experimental Data Relating to the Cationic Amino Acids

A composition according to the invention resulting directly from the experimental protocol carried out in the example provided and a composition obtained by virtue of a protocol modified in that a composition containing only the three cationic amino acids (Arg-Lys-His) had been substituted for the composition of the 12 essential amino acids were compared with regard to the nonadsorbed amount of PRP-T at the end. No difference in the amount of nonadsorbed PRP-T was observed, thereby showing that only the cationic amino acids are important.

The invention claimed is:

1. A method for preparing a liquid vaccine combination comprising at least:
   aluminum oxide hydroxide (AlOOH),
   one hepatitis B surface antigen (HBsAg),
   one *Haemophilus influenzae* type b (Hib) antigen consisting of capsular polysaccharide conjugated to a carrier protein,
   in which the hepatitis B surface antigen is kept adsorbed on AlOOH, whereas the Hib antigen is kept nonadsorbed, wherein:
      the hepatitis B surface antigen is adsorbed onto AlOOH in order to obtain an AlOOH/HBsAg complex,
      said AlOOH/HBsAg complex is mixed with the Hib antigen in the presence of cationic amino acids at a concentration of at least 100 mg/l and at most 2 mg/ml and of phosphate ions at a concentration of 35 to 45 mMol/l.

2. The method as claimed in claim 1, wherein the HBsAg antigen is adsorbed onto the aluminum by mixing a suspension of AlOOH with a suspension of HBsAg with stirring for at least 4 hours.

3. The method as claimed in claim 1, characterized in that the cationic amino acids are added to said AlOOH/HBsAg complex before the mixing with the Hib antigen.

4. The method as claimed in claim 1, characterized in that the cationic amino acids are added to said Hib antigen before the mixing with the AlOOH/HBsAg complex.

5. The method as claimed in claim 1, characterized in that the phosphate ions are added to said AlOOH/HBsAg complex before the mixing with the Hib antigen.

6. The method as claimed in claim 1, characterized in that the pH of the preparation comprising the AlOOH/HBsAg complex is adjusted to 7.1±0.1 before the mixing with the Hib antigen.

7. The method as claimed in claim 1, further comprising:
   preparing a composition comprising at least one antigen chosen from diphtheria, tetanus, polio and whooping cough antigens, and also aluminum oxide hydroxide, and
   mixing said AlOOH/HBsAg complex with said composition, before carrying out the mixing with the Hib antigen.

8. The method as claimed in claim 7, wherein said composition is prepared by adding each of the antigens successively to a suspension of aluminum oxide hydroxide and by stirring between each addition of antigens.

9. The method as claimed in claim 1, characterized in that:
   the HBsAg is adsorbed onto a partial amount of AlOOH representing one third of the total AlOOH present in the final composition, for a period of 20 to 24 hours, in order to form an AlOOH/HBsAg complex,
   in parallel, the following are successively adsorbed onto an additional amount of AlOOH: diphtheria toxin D, tetanus toxin T, *Bordetella pertussis* purified toxin PTxd, itself preadsorbed onto AlOOH, and *Bordetella pertussis* filamentous hemagglutinin FHA, itself preadsorbed onto AlOOH, then phosphate ions are added thereto, then the AlOOH/HBsAg complex is added thereto,
   phosphate ions are again added in an amount which makes it possible to achieve a concentration of 40 mMol/l in the final composition,
   at least one cationic amino acid is added in an amount which makes it possible to achieve a concentration of at least 100 mg/l in the final composition,
   the pH is adjusted to 7.1±0.1,
   polio antigens in the form of inactivated type 1 and/or type 2 and/or type 3 viruses are added,
   the Hib antigen is added,
   the pH is adjusted to 7.1±0.1,
   the composition obtained is distributed into syringes or into bottles.

10. The method as claimed in claim 1, characterized in that at least 250 l of vaccine composition are prepared on an industrial scale.

11. The method as claimed in claim 1, wherein the HBsAg antigen is adsorbed onto the aluminum by mixing a suspension of AlOOH with a suspension of HBsAg with stirring for at least 12 hours.

12. The method as claimed in claim 1, wherein the HBsAg antigen is adsorbed onto the aluminum by mixing a suspension of AlOOH with a suspension of HBsAg with stirring between 20 and 24 hours.

* * * * *